United States Patent
Silva et al.

(10) Patent No.: US 9,814,380 B1
(45) Date of Patent: Nov. 14, 2017

(54) PEDICLE ENDOSCOPE

(71) Applicants: Octavio Cesar Silva, Melbourne, FL (US); Fernando Emilio Silva, Fort Worth, FL (US)

(72) Inventors: Octavio Cesar Silva, Melbourne, FL (US); Fernando Emilio Silva, Fort Worth, FL (US)

(*) Notice: Subject to any disclaimer, the term of this patent is extended or adjusted under 35 U.S.C. 154(b) by 199 days.

(21) Appl. No.: 14/839,961

(22) Filed: Aug. 29, 2015

Related U.S. Application Data

(63) Continuation-in-part of application No. 13/783,292, filed on Mar. 2, 2013, now abandoned.

(51) Int. Cl.
| | | |
|---|---|---|
| *A61B 1/313* | (2006.01) | |
| *A61B 1/06* | (2006.01) | |
| *A61B 1/04* | (2006.01) | |
| *A61B 1/00* | (2006.01) | |
| *A61B 1/015* | (2006.01) | |

(52) U.S. Cl.
CPC .......... *A61B 1/3135* (2013.01); *A61B 1/0011* (2013.01); *A61B 1/00167* (2013.01); *A61B 1/015* (2013.01); *A61B 1/0676* (2013.01)

(58) Field of Classification Search
CPC ... A61B 1/00165; A61B 1/00071; A61B 1/07; A61B 1/315; A61B 1/0011; A61B 1/00167; A61B 1/015; A61B 1/00073
See application file for complete search history.

(56) References Cited

U.S. PATENT DOCUMENTS

| | | | |
|---|---|---|---|
| 3,776,222 A | 12/1973 | Smiddy | |
| 4,024,858 A | 5/1977 | Chikama | |
| 4,826,280 A | 5/1989 | Tsuno | |
| 2003/0216618 A1* | 11/2003 | Arai | A61B 1/00163 600/178 |
| 2006/0173242 A1* | 8/2006 | Navok | A61B 1/0011 600/133 |
| 2006/0229497 A1* | 10/2006 | Toyama | A61B 1/00091 600/156 |
| 2012/0215065 A1* | 8/2012 | Mukherjee | A61B 1/042 600/108 |
| 2013/0060087 A1* | 3/2013 | Yoshida | A61B 1/00045 600/112 |
| 2017/0065287 A1* | 3/2017 | Silva | A61B 17/1671 |

* cited by examiner

*Primary Examiner* — Daniel J Colilla

(57) ABSTRACT

The Pedicle Endoscope represents a new way to image the insertion of screws in vertebrae with the aid of fiber optics. The endoscope can operate in the visible and infrared spectra and is used in conjunction with a polyaxial or multiaxial screwdriver assembly. The mechanical assembly is comprised of a screwdriver, a polyaxial or multiaxial shaft, and a pedicle screw. The polyaxial shaft is inserted in the screwdriver and this assembly couples with the pedicle screw. Once this mechanical assembly is integrated, the endoscope is inserted through a bore that runs along the polyaxial shaft and the pedicle screw and it comes out of the screw tip, imaging the progression of the screw as it penetrates the incision in the vertebra. The endoscope consists of three fiber cores, one for imaging and two for illumination and a conduit for irrigation and air suction. Externally, the fiber cores and the conduit terminate in a fiber bundle that connects the imaging fibers to an imaging device, the illumination fibers to an illumination source and the conduit to an irrigation or suction device.

5 Claims, 20 Drawing Sheets

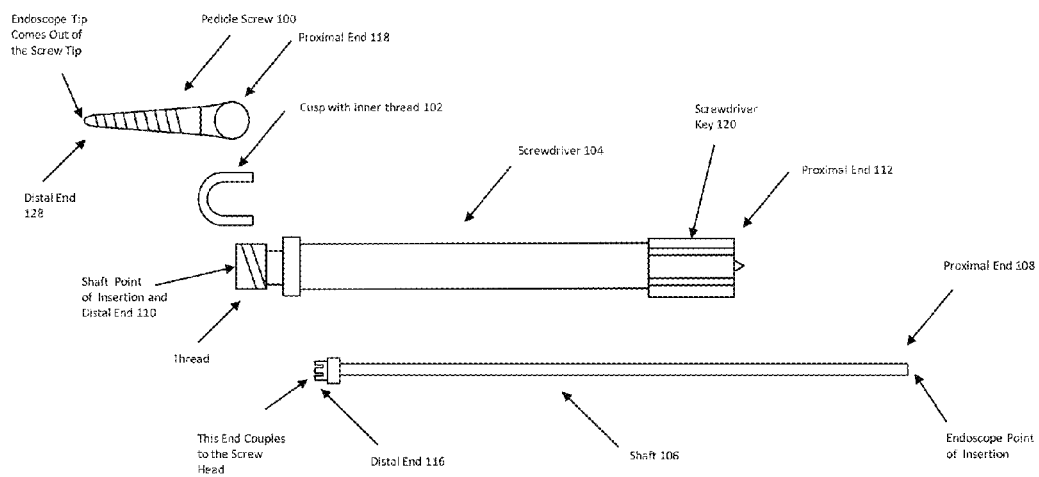
Figure 1. Pedicle Screw Integrated Mechanical Assembly (Not to Scale)

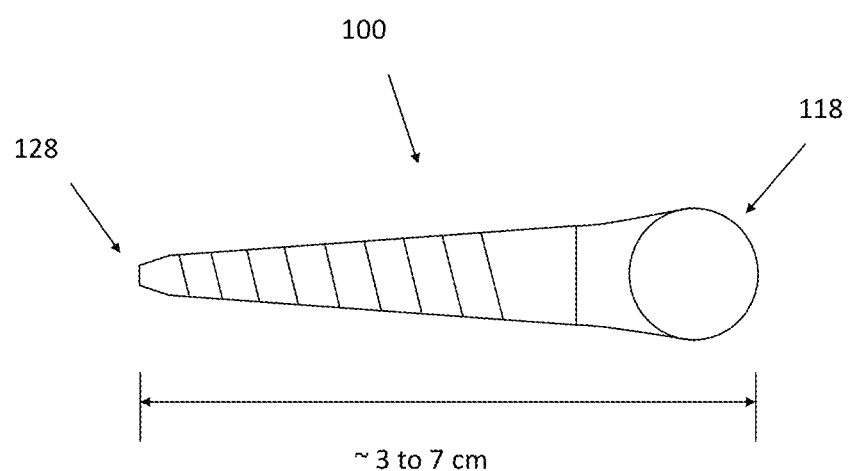
Figure 2. Pedicle Screw Side View (Not to Scale)

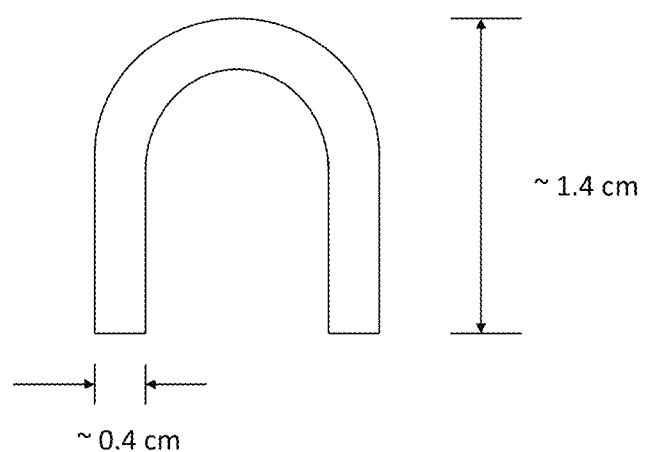
Figure 3. Cusp Side View (Not to Scale)

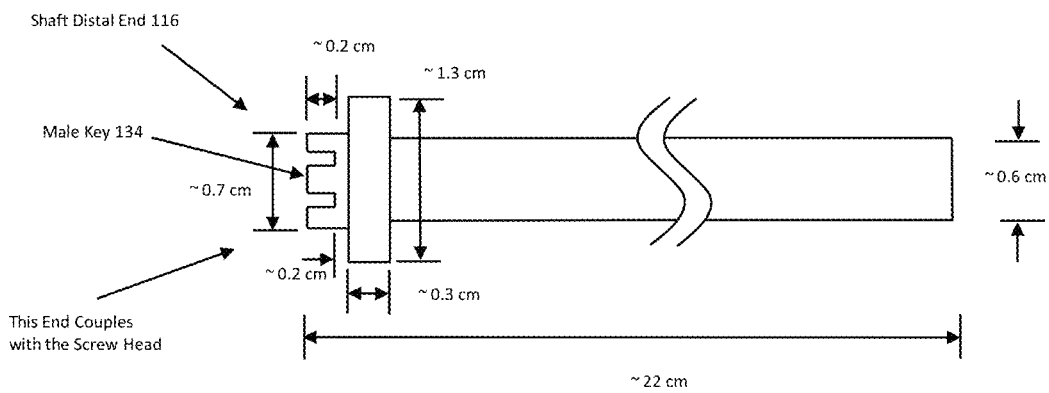
Figure 4. Side View of the Shaft (Not to Scale)

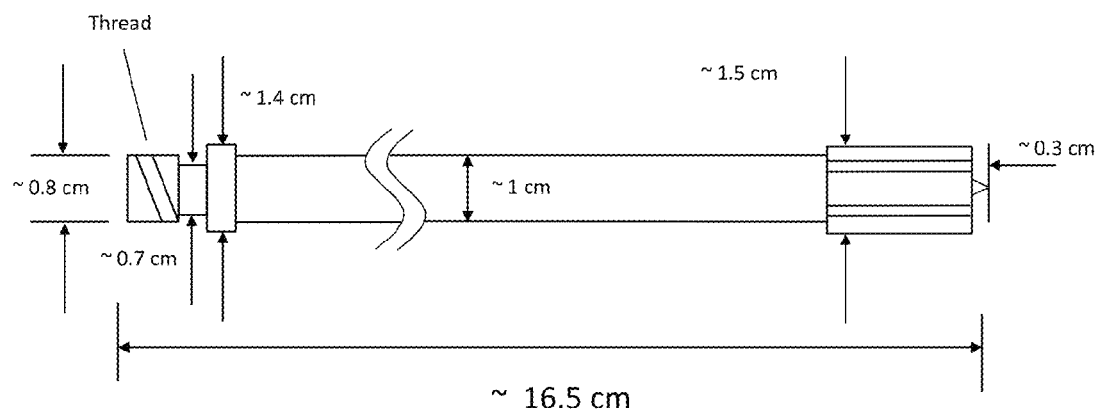
Figure 5. Side View of Screwdriver (Not to Scale)

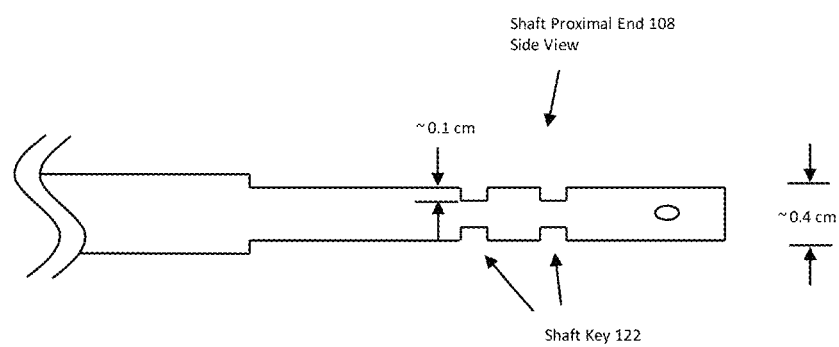
Figure 6. Proximal End of Shaft (Not to Scale)

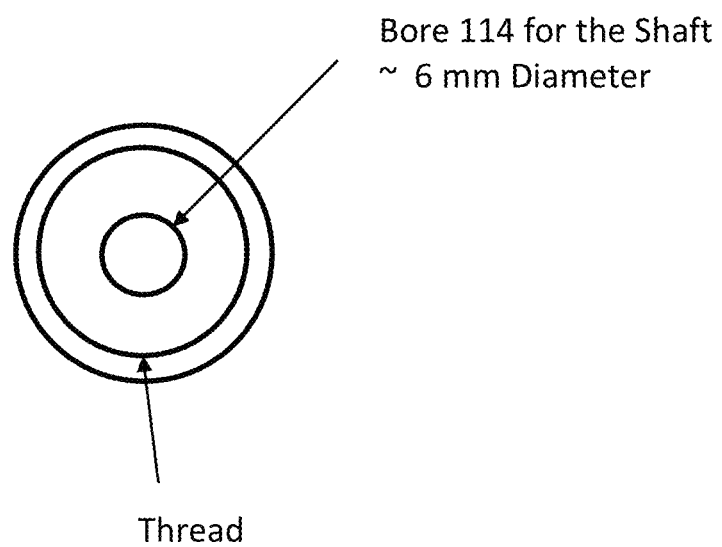
Figure 7. Screwdriver Distal End Front View (Not to Scale)

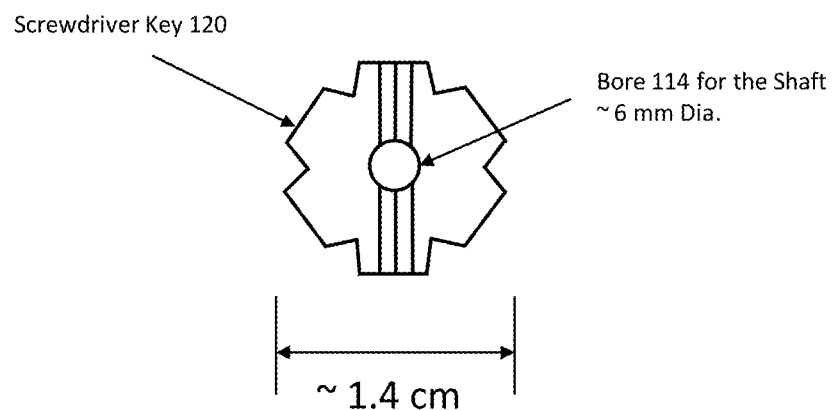
Figure 8. Proximal End View of Screwdriver (Not to Scale)

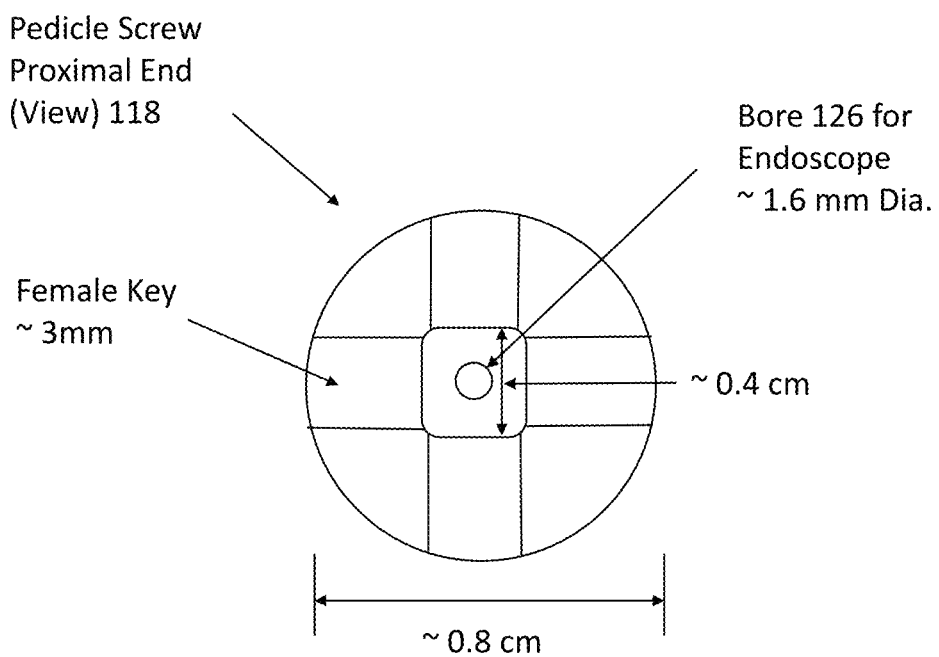
Figure 9. Head View of the Pedicle Screw (Not to Scale)

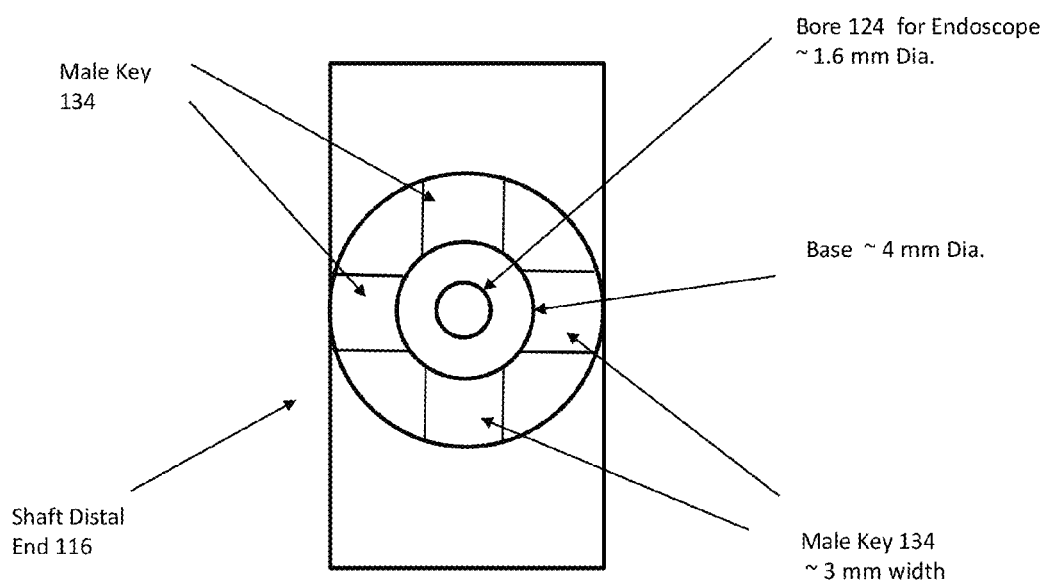
Figure 10. Distal End View of the Shaft (Not to Scale)

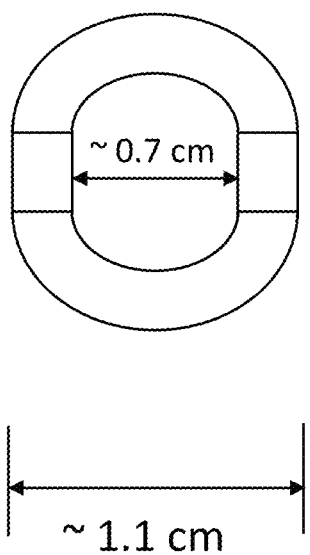
Figure 11. Cusp Front View (Not to Scale)

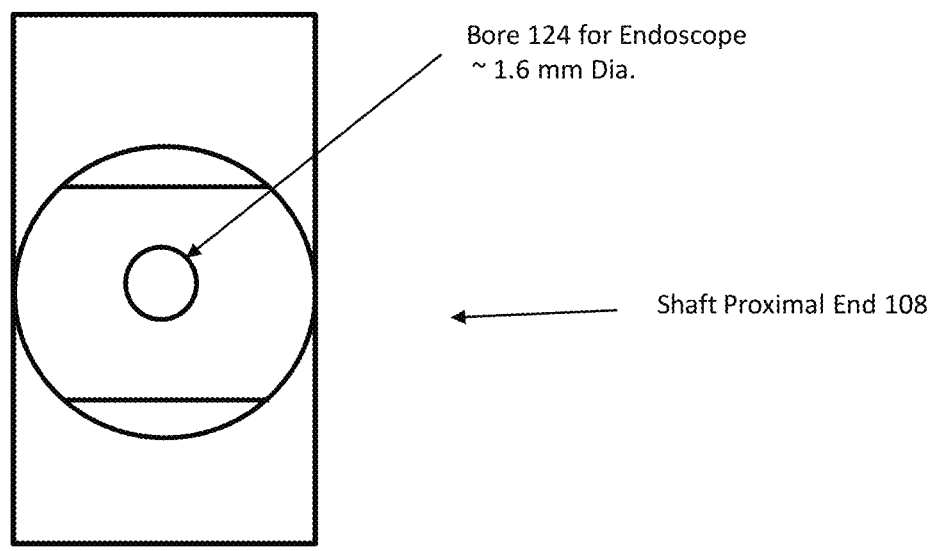
Figure 12. Proximal End View of the Shaft (Not to Scale)

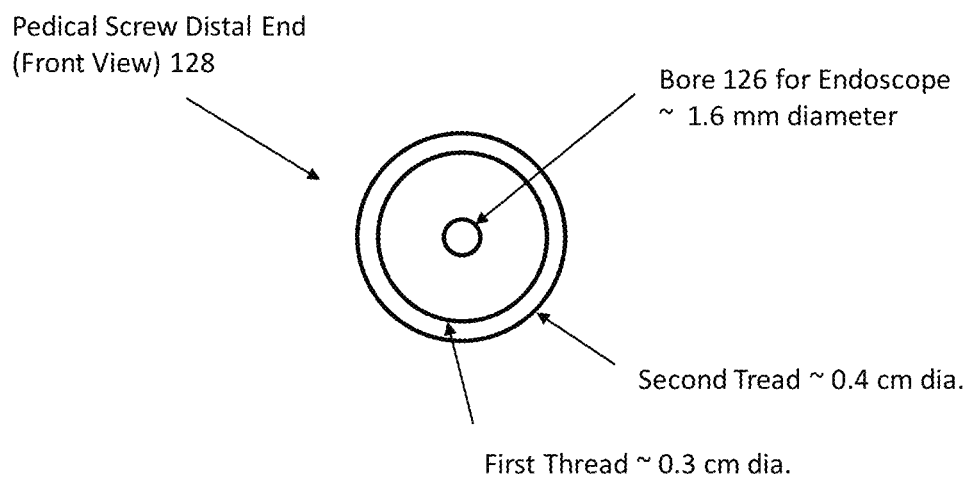
Figure 13. Pedicle Screw Tip View (Not to Scale)

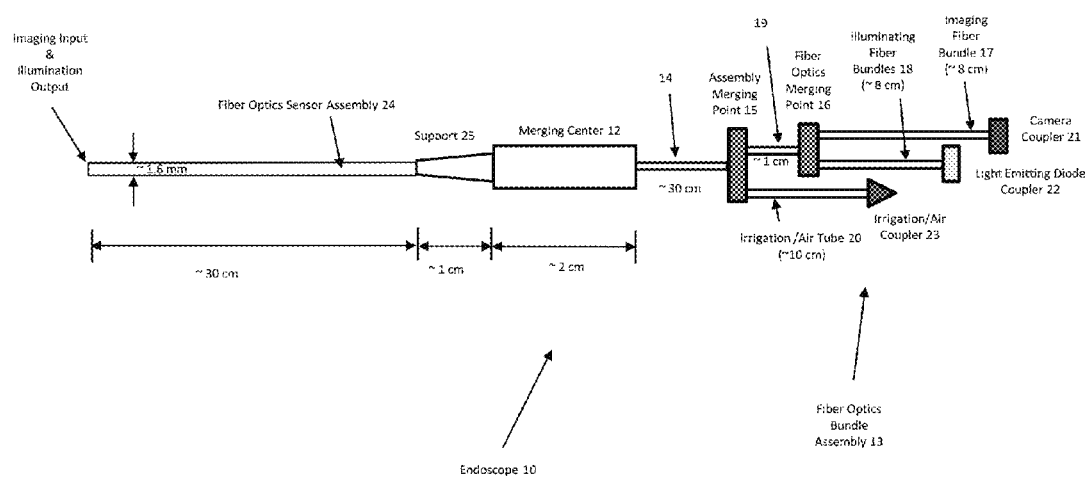
Figure 14. Endoscope Architecture (Not to Scale)

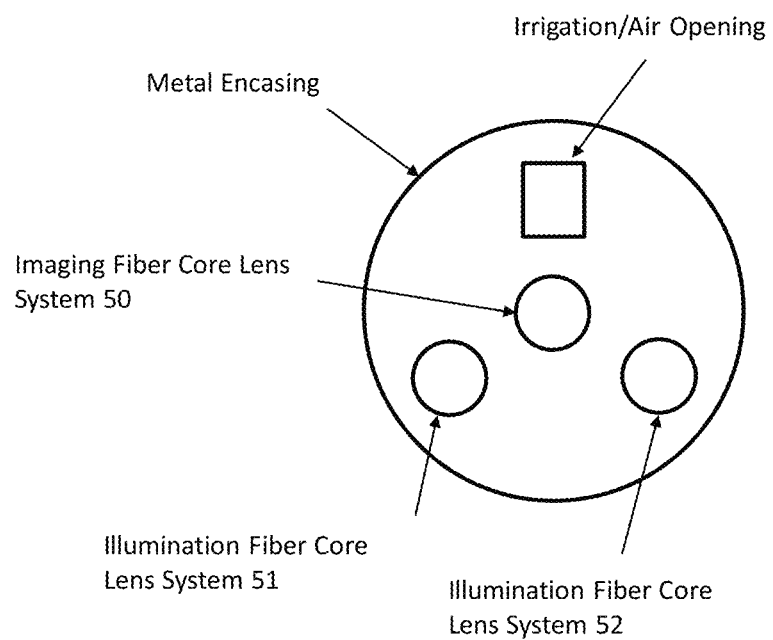
Figure 15. Distal Tip of Endoscope (Not to Scale)

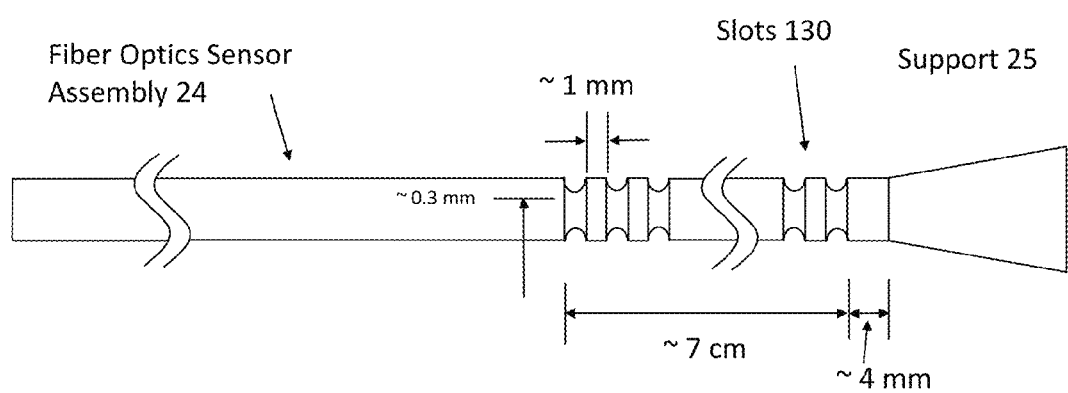
Figure 16. Layout of Endoscope Slots (Not to Scale)

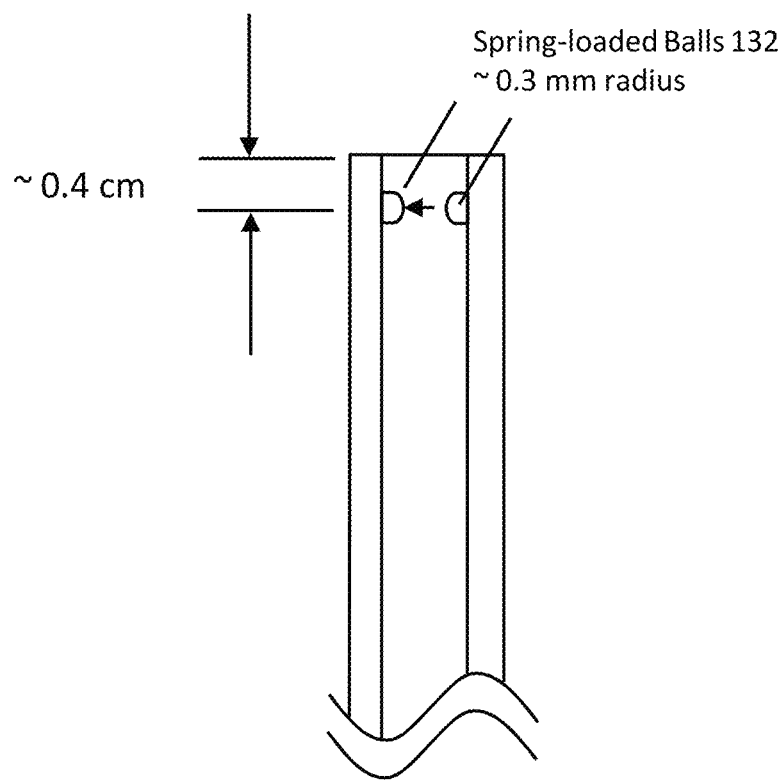
Figure 17. Cross Section of the Shaft (Not to Scale)

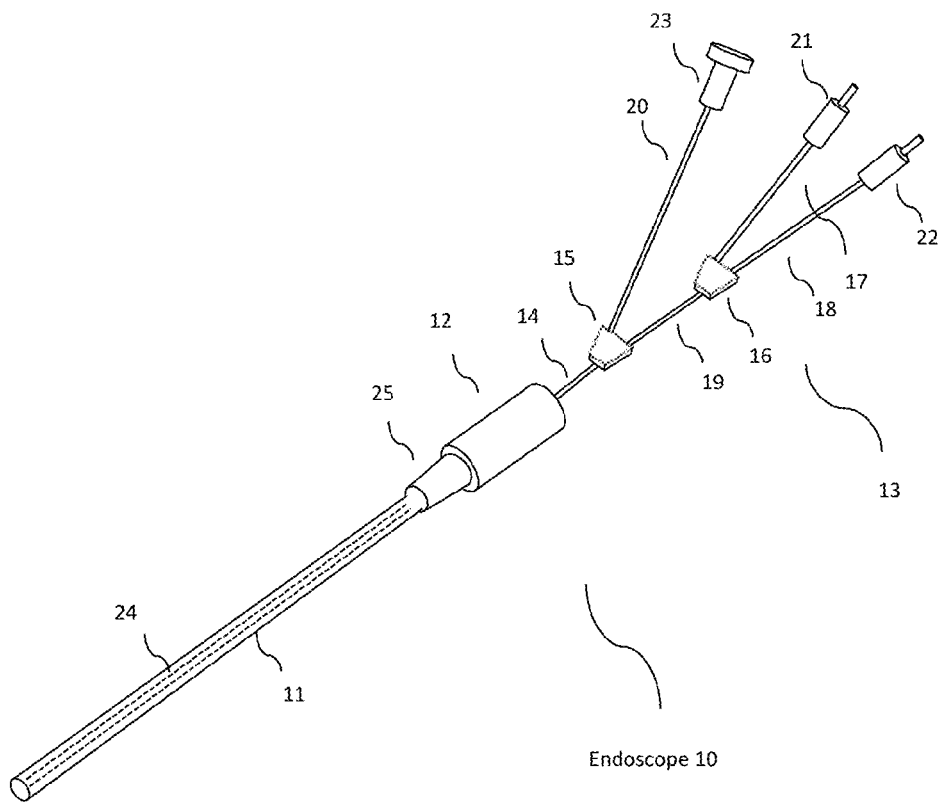
Figure 18. Three-Dimensional Representation of the Endoscope (Not to Scale)

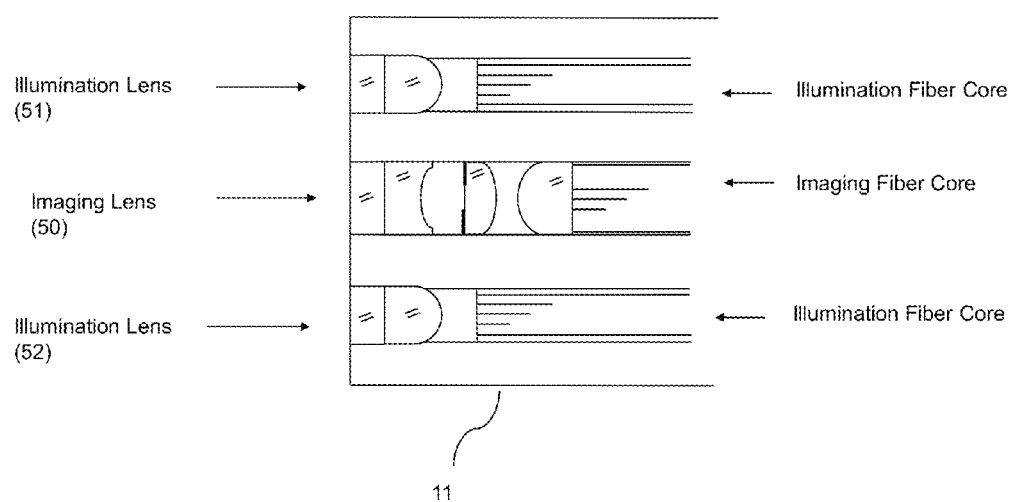
Figure 19. Typical Representation of the Endoscope Distal End – Top View (Not to Scale)

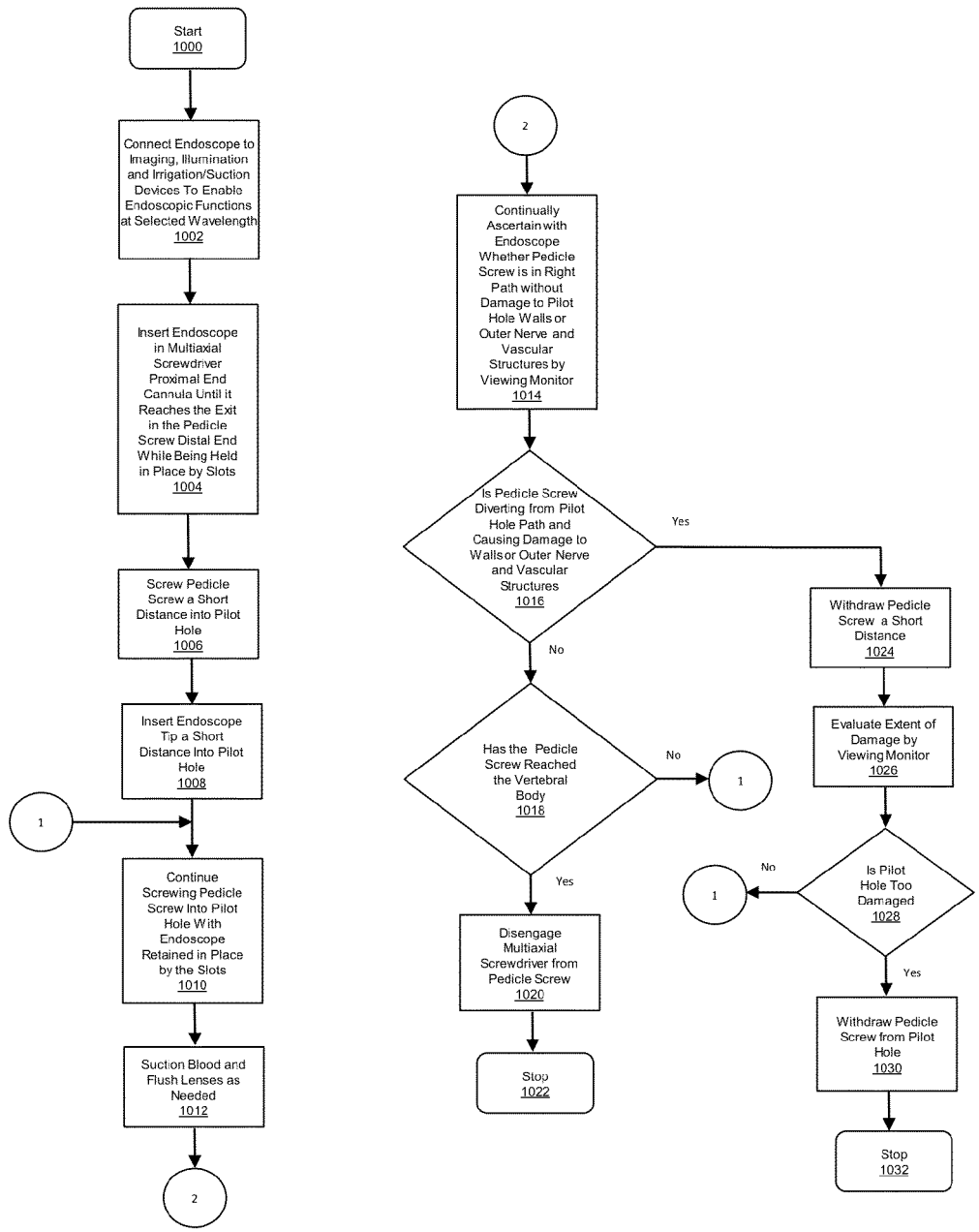
Figure 20. Generalized Method to Inspect Pilot Holes for Pedicle Screw Insertion

PEDICLE ENDOSCOPE

CROSS REFERENCE TO RELATED APPLICATIONS

The present specification is a continuation-in-part application of non-provisional patent application Ser. No. 13/783,292 which corresponds to provisional patent application Ser. No. 14/431,047.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not Applicable.

DESCRIPTION OF DRAWINGS

FIG. 1 shows the integrated mechanical assembly. It consists of a pedicle screw, a cusp that couples with the screw, a polyaxial screwdriver and a shaft that is inserted in the screwdriver.

FIG. 2 shows the side view of the screw.

FIG. 3 shows the cusp side view.

FIG. 4 shows the side view of the shaft.

FIG. 5 shows the screwdriver side view.

FIG. 6 shows the proximal end of the shaft.

FIG. 7 shows the distal end view of the screwdriver.

FIG. 8 shows the screwdriver proximal end view.

FIG. 9 shows the head of the screw.

FIG. 10 shows the shaft distal end view.

FIG. 11 shows the cusp front view.

FIG. 12 shows the proximal end view of the shaft. The shaft front key is not shown.

FIG. 13 shows the tip view of the screw.

FIG. 14 shows the overall architecture of the endoscope. The device provides an external interface to an imaging device that provides an electrical signal to a monitor to view real time video and images. It also provides interfaces to an illumination device and to an irrigation/air suction device.

FIG. 15 shows the layout of the tip of the fiber optics assembly. It has three fiber optics cores, two for illumination and one for imaging. It also has a conduit for irrigation or air suction.

FIG. 16 shows the slots in the endoscope to which the spring-loaded balls in the shaft snap.

FIG. 17 shows a cutaway view of the shaft. The spring-loaded balls are shown near the end.

FIG. 18 shows a three-dimensional representation of the endoscope.

FIG. 19 shows a typical distal optical lens system design.

FIG. 20 shows a generalized method to monitor pedicle screw insertion.

SUMMARY OF THE INVENTION

The Pedicle Endoscope represents a new way to image the insertion of screws in vertebrae with the aid of fiber optics. Presently, a trial and error method is used to insert the screw. Before inserting the screw, a hole is bored in the vertebra with a pick device. Then a thread is created with a tap and the screw is inserted in some cases by probing the vertebra hole with the aid of a small diameter rod that runs along a conduit in the screw. The fiber optics endoscope replaces the rod and images the progression of the screw insertion in the vertebra incision.

DETAILED DESCRIPTION OF THE INVENTION

The endoscope allows a surgeon to monitor the progression of the insertion of pedicle screws in pedicle pilot holes so that screws can serve as spine anchor points for stabilizing rods. The endoscope is inserted in the polyaxial or multiaxial screwdriver bore or canula in the proximal end thereby allowing the endoscope distal end to come out of the pedicle screw distal end when the screw is engaged to the polyaxial or multiaxial screwdriver. The endoscope allows surgeons to inspect pilot holes in great detail as the pedicle screws are screwed into pilot holes. This method is unique since by choosing the proper light wavelength tissue becomes transparent allowing a surgeon to inspect the pilot hole walls and their thinness, the nerve and vascular structures located outside the pedicle bone as well as to avoid pilot hole wall breaches with the pedicle screw. Light in the visible spectrum, for example at blue or green wavelengths or white light for that matter, can only be used to inspect the pilot hole walls to look for roughness since light in the visible spectrum cannot penetrate bone tissue virtually. However, penetration of bone tissue can be achieved at infrared wavelengths notably in the near infrared spectrum region where penetrations can be of the order of 3 to 4 cm. Other infrared regions, for example short or mid wave infrared spectrum, allow similar penetrations at longer wavelengths where windows of low attenuation exist, for example at 1600 nm. Since the diameter of the pedicle is less than 2 cm, inspection of nerve and vascular structures outside of the pedicle bone is possible when the infrared light is intense. Therefore, not only can the surgeon inspect the pilot hole walls but also see beyond them as they become transparent and predict before hand whether the screw is going to breach the pilot hole wall and is following a path toward outer nerve and vascular structures located next to the outer surface of the pedicle bone. This operation can be viewed in real-time in a video monitor such that the pedicle screws can be screwed precisely to the pilot hole walls while avoiding damage to these walls and vital outer nerve and vascular structures.

FIG. 20 describes a generalized method to inspect pilot holes in pedicles with the endoscope as the pedicle screws are inserted. The endoscope is connected to imaging, illumination and irrigation/suction devices to enable its endoscopic functions at the selected wavelengths in the visible and infrared spectrum 1002. The endoscope is inserted in the polyaxial or multiaxial screwdriver proximal end canula until it reaches the exit in the pedicle screw distal end while being held in place by the slots 1004. The pedicle screw is screwed a short distance into pilot hole 1006. The endoscope tip is inserted a short distance into the pilot hole 1008. The pedicle screw screwing is continued into pilot hole with the endoscope retained in place by the slots 1010. Blood is suctioned and endoscope lenses flushed as needed 1012. Continually ascertain with endoscope whether pedicle screw is in the right path without damage to pilot hole walls or outer nerve and vascular structures by viewing monitor 1014. A determination is made whether pedicle screw is diverting from pilot hole path and causing damage to walls or outer nerve and vascular structures 1016. If so, the pedicle screw is withdrawn a short distance 1024. The extent of the damage is evaluated by viewing monitor 1026. A determination is made whether pilot hole is too damaged 1028. If so, the pedicle screw is withdrawn 1030 and the operation is stopped 1032. If in step 1028 there is no damage, the operation continues to process step 1010. If the determination in process step 1016 is negative another determination is made whether the vertebral body has been reached 1018. If so, the polyaxial or multiaxial screwdriver is disengaged from the pedicle screw 1020 and the operation is stopped 1022 with success. If the vertebral body has not been reached in determination 1018, the operation continues to process step 1010.

In addition, before the pedicle screw is inserted in the pilot hole, the Pedicle Endoscope can be used to inspect the pilot hole for suitability of such insertion. In this case, the endoscope does not need to be engaged into the canula of the polyaxial or multiaxial screwdriver since this is a stand-alone operation. The endoscope alone can be inserted into the pilot hole to determine whether it is structurally suitable for the subsequent insertion of the pedicle screw. The endoscope, at infrared wavelengths, can see beyond the pilot hole walls and determine their thinness with respect to the outer surface of the pedicle bone. This way the endoscope can determine whether the outer nerve and vascular structures can be compromised during the subsequent operation of inserting the pedicle screw.

Other applications of the endoscope include active imaging of other anatomy structures. For example, at infrared wavelengths, the endoscope can be used to determine the structure of subcutaneous tumors by operating it next to the skin where the malformation is located. Similarly, the infrared endoscope can be used to see through other tissues include bone tissue to determine the condition of anatomical structures.

The pedicle screw assembly is shown in FIGS. 1, 2, 3, 4 and 5. The mechanical assembly consists of a pedicle screw 100, a cusp 102, a screwdriver 104 and a shaft 106. The shaft proximal end 108 (FIG. 6) is inserted in the screwdriver hole 114 in the distal end 110 (FIG. 7) which screws to the cusp 102. The shaft 106 comes out of the proximal end 112 of the screwdriver 104 through the bore 114 shown in FIG. 8. The shaft 106 has a key design 134 in the distal end 116 to couple with the pedicle screw head 118 as shown in FIGS. 9, 4 and 10. The screw head 118 snaps to the cusp 102 shown in FIGS. 3 and 11. The cusp 102 rotates around the screw head 118 and has an inner thread that screws to the screwdriver distal end 110 with the shaft 106 inserted in the screwdriver 104. The screwdriver 104 and shaft 106 have keys, 120 and 122, respectively, in the proximal end as shown in FIGS. 6 and 8 to which the screwdriver handle (not shown) snaps.

Once the mechanical assembly is put together, the endoscope is inserted in the shaft proximal end 108. The shaft 106 and the screw 100 have bore, 124 and 126, respectively, along their lengths through which the endoscope passes. The bore 124 in the proximal end 108 of the shaft 106 is shown in FIG. 12. The tip 128 view of the screw 100 is shown in FIG. 13, and the view of the screw head 118 (proximal end) is shown in FIG. 9.

As shown in FIG. 14 and FIG. 18, the endoscope 10 consists of metal tubing 11 that encases three fiber cores through an internal channel 24 that runs along its length. These fiber cores connect externally to their respective fiber bundles in the fiber optics bundle assembly 13 (i.e. the imaging fiber core connects to the imaging fiber bundle 17 and the illumination fiber cores to the illumination fiber bundles). The two illumination fiber cores carry light from an illumination source that can operate in the visible or infrared spectrum and that is connected to the illumination fiber bundles 18 through an optical coupling that connects to connector 22. At the output of the fiber optics assembly tip, these two fiber cores, through their optical lens systems, illuminate the pilot hole in the vertebra. The other imaging fiber core carries the imaging of the insertion operation. The imaging is carried to an imaging device that can operate in the visible or infrared spectrum and that connects to the imaging fiber bundle 17 through connector 21. The tip layout of the fiber optics assembly is shown in FIG. 15. In addition to the fiber cores, the assembly tubing contains a conduit for irrigation and air suction.

The endoscope is inserted in the shaft 106 through the proximal end 108 and comes out of the tip 128 of the pedicle screw 100 on the other end. The endoscope outer metal tubing has slots 130, as shown in FIG. 16, that snap to the spring-loaded balls 132 in the shaft bore 124. FIG. 17 shows a cutaway section of the shaft 106 with the spring-loaded balls 132 inside. FIGS. 6 and 12 show views of the shaft proximal end 108.

The fiber bundle assemblies that couple to the merging center 12 contain two merging points as shown in FIG. 14. The first merging point 16 merges the fiber bundles that carry illumination 18 and the imaging 17. The resulting fiber bundle 19 then merges with the irrigation/air suction conduit 20 at the second merging point 15 to form a single wire 14 that penetrates the merging center 12. After they enter the merging center 12, the illumination and imaging fiber bundles continue extending into their respective fiber cores in the fiber optics assembly. The irrigation/air conduit also continues in the fiber optics assembly and terminates at the tip as shown in FIG. 15.

The fiber optics assembly has integrated imaging lens system 50 and illumination lens systems 51 and 52 at the distal end that couple to the integrated fiber cores at the tip. The imaging lens system 50 at this distal end is such that objects can be focused from approximately 2 mm to any given distance. On the other end, the fiber optics bundles provide the lens systems interface to the visible or infrared imaging device optical assembly and the visible or infrared imaging device, respectively. This is shown in FIG. 14.

The imaging fiber core consists nominally of 10,000 fibers and continues to a fiber bundle external to the merging center 12. This imaging fiber bundle 17 terminates in a coupler 21 that interfaces to an optical assembly with an integrated imaging device to image the vertebra incision. The camera provides an electrical signal to a monitor to provide images to medical personnel.

The endoscope 10 also provides an optical lens system interface connector 22 to a visible or infrared illumination source. The illumination source illuminates the incision by transmitting light through the illumination fiber bundles 18 and the illumination fiber cores in the metal tubing. Thus, the illumination source interfaces with the illumination fiber bundles 18 that merge with the imaging fiber bundle 17 before they enter the merging center 12. The illumination bundles 18 enter the merging center 12 to provide two illumination fiber cores in the integrated fiber optics assembly. The illumination fiber cores consist nominally of 10,000 fibers each. At the distal end, the endoscope 10 provides an illumination lens system, 51 or 52, for each illumination fiber core to provide uniform illumination for the imaging fiber core field of view.

The imaging device can be of the CCD or CMOS type or any other device suitable for operation in the infrared spectrum, including the near, short wave or mid wave infrared spectrum. Similarly, the illumination source could be a light emitting diode (LED), an infrared LED or an infrared laser suitable for operation in a given region of the infrared spectrum.

The other external interface connector 23 is to an irrigation device or to a suction device.

The mechanical assembly design is similar to existing patented designs. One modification is the integration of the spring-loaded balls 132 in the shaft 106.

Likewise, the endoscope 10 design is similar to existing patented designs. In these designs, the thickness of the metal encasing 11 needs to increase to accommodate the slots 130 and the fiber optics metal tubing is longer.

The design of flexible endoscopes has been documented throughout the literature. A number of expired patents describe the use of fiber optics bundles to carry light to illuminate a desired surgical region and to carry imaging of that site. These patents also describe endoscopic designs with adjunct irrigation and suction conduits to help clean the optics distal end form debris in the surgical region. A similar design of the fiber optics bundle is described in U.S. Pat. No. 4,024,858 Toshio Chikama, May 24, 1977. The inner tubes in FIG. 2 can accommodate illumination and imaging fiber bundles as well as irrigation and suction conduits. Another design is described in U.S. Pat. No. 3,776,222, by Joseph F. Smiddy, Dec. 4, 1973. The patent describes an endoscope for viewing a medical operation by means of a fiber optics bundle as shown in FIG. 2, 32.

A similar design of the fiber optics bundle is described in U.S. Pat. No. 4,826,280 Koichi Tsuno, et al, May 2, 1989. The prior art conventional endoscope design described by Tsuno provides connectors to imaging, illumination and irrigation devices. This is shown in FIG. 1 (items 7, 6, 9). The fiber bundles merge at a junction point and further merge with the irrigation channel at junction 5.

The basic endoscope design as described in the paragraphs above is claimed in U.S. patent application Ser. No. 13/731,070. Thus, that patent application describes the architecture of the imaging fiber core, the illumination fiber cores and irrigation/suction conduit in the cylindrical metal tubing 11 and their continuation in the fiber optics bundle assembly 13 with the respective connectors to an imaging device 21, LED assembly 22 and irrigation/suction devices 23. In addition as shown in FIG. 19, that patent application describes representative imaging optical lens system and illumination optical lens systems in the optical distal end located in the distal end of the metal tubing 11.

The endoscope described herein can be operated in the visible and infrared (IR) light spectrum although operation in each part of the spectrum entails the use of the appropriate imaging and illumination devices and integration of the same.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

The invention claimed is:

1. An endoscope configured for monitoring the progression of the insertion of pedicle screws in pedicle pilot holes and to image said pilot holes to determine their condition and thinness, and to determine said pilot hole wall breaches by said pedicle screws and the location of outer nerve and vascular structures in the pedicle by operation at selected visible and infrared light wavelengths,
 wherein said endoscope is inserted in the proximal end of a multiaxial screwdriver cannula;
 wherein said multiaxial screwdriver engages a pedicle screw with a cannula at its distal end;
 wherein said multiaxial screwdriver is configured with spring-loaded balls near a proximal end in an inner wall of the cannula of the multiaxial screwdriver;
 wherein said endoscope can exit said pedicle screw distal end through said pedicle screw cannula, the endoscope comprising:
 an elongated cylindrical metal body structure having a proximal end and a distal end, wherein said distal end terminates on a plane perpendicular to said elongated cylindrical metal body axis;
 a cylindrical merging center structure of a predetermined length, configured for use as a handle and attached to said elongated cylindrical metal body proximal end by a conical support structure;
 a fiber optics bundle assembly that enters said cylindrical merging structure as a single wire;
 endoscope slots near the proximal end of the elongated cylindrical metal body structure, wherein the endoscope slots engage the spring-loaded balls in the inner wall of the cannula of the multiaxial screwdriver;
 wherein said elongated cylindrical metal body structure is configured with a length and a diameter to traverse the cannula of the multiaxial screwdriver, the cannula of the pedicle screw, and the length of the pilot hole;
 wherein said endoscope is configured further with a length and a diameter to enter and inspect the pilot hole from the opening of the pilot hole in the pedicle bone to the end of the pilot hole near the vertebra center, before the insertion of the pedicle screw in the pilot hole, for wall roughness or fractures by operation in the visible and infrared spectra, the thinness of the pilot hole walls and the proximity of the pedicle bone outer vascular and nerve structures by operation in the infrared spectrum to determine the suitability of the pilot hole for subsequent pedicle screw insertion, using the multiaxial screwdriver, wherein the infrared wavelengths that the endoscope operates in includes the near infrared, the short wave infrared spectrum, the mid wave infrared spectrum, or the long infrared spectrum.

2. The endoscope in claim 1 further comprised of:
 an imaging system that runs along the longitudinal axis of said elongated cylindrical metal body structure;
 two illumination systems longitudinally parallel to and below the axis of said elongated cylindrical metal body structure located toward the periphery;
 an irrigation and suction conduit;
 wherein the imaging system and illumination systems are terminated in an optical distal end placed geometrically flush on said elongated cylindrical metal body structure distal end;
 wherein the imaging system is comprised of an imaging fiber bundle terminated in an objective lens system;
 wherein each illumination system is comprised of an illumination fiber bundle terminated in an illumination lens system;
 where the objective lens system is located at the central axis of said cylindrical body structure;
 wherein each illumination lens system is located below the central axis of said elongated cylindrical body structure toward the periphery of the elongated cylindrical metal body structure and oppositely placed with respect to the other illumination lens system to provide uniform and intense illumination of the pilot hole channel and the external outer periphery of the pedicle bone at said infrared wavelengths; and wherein the irrigation and suction conduit are placed above the illumination system to end at an opening above the objective lens system.

3. The endoscope in claim 2 wherein said fiber optics bundle assembly is comprised of an imaging fiber bundle encased in a plastic housing, two illumination fiber bundles encased in a plastic housing, and an irrigation and suction conduit;

wherein the imaging fiber bundle merges with the two illumination fiber bundles at a plastic-molded junction to merge in a fiber optics assembly that encases individually the imaging fiber bundle and the two illumination fiber bundles in a synthetic material;

wherein the irrigation and suction conduit further merges with said fiber optics assembly at a plastic-molded junction to merge in an integrated housing that encases individually the imaging fiber bundle, the two illumination fiber bundles and the irrigation and suction conduit in a synthetic material and enters said cylindrical merging structure as said single wire;

wherein said imaging fiber bundle in said fiber optics bundle assembly transitions to said imaging system in said elongated cylindrical metal body structure as the same imaging fiber bundle to provide imaging functions by connecting an imaging device to the proximal end of said fiber optics bundle assembly though one connector;

wherein each illumination fiber bundle in the fiber optics bundle assembly further transitions to its corresponding illumination system in said elongated cylindrical metal body structure to provide illumination functions by connecting an illumination device at the proximal end of said fiber optics bundle assembly through one connector;

wherein the irrigation and suction conduit in said fiber optics bundle assembly further transitions to said irrigation and suction conduit in said elongated cylindrical metal body structure to provide irrigation and suction functions by connecting irrigation and suction devices at the proximal end of said fiber optics bundle assembly through one connector; and wherein the imaging and illumination fiber optics bundles and the irrigation and suction conduit are flexible to allow for unobstructed manipulation of the endoscope with the handle.

4. A method for providing imaging to monitor the progression of the insertion of pedicle screws in pedicle pilot holes with an endoscope, wherein said endoscope comprises:

an elongated cylindrical metal body structure having a proximal end and a distal end, wherein said distal end terminates on a plane perpendicular to said elongated cylindrical metal body axis;

a cylindrical merging structure of a predetermined length, configured for use as a handle and attached to said elongated cylindrical metal body proximal end by a conical support structure;

a fiber optics bundle assembly that enters said cylindrical merging structure as a single wire;

wherein said elongated cylindrical metal body structure is configured with a length and a diameter to traverse the cannula of the multiaxial screwdriver, the cannula of the pedicle screw and the length of the pilot hole;

wherein the endoscope is further comprised of:

an imaging system that runs along the longitudinal axis of said elongated cylindrical medal body;

two illumination systems longitudinally parallel to and below the axis of said elongated cylindrical medal body located toward the periphery; an irrigation and suction conduit;

wherein the imaging system and illumination systems are terminated in an optical distal end placed geometrically flush on said elongated cylindrical metal body distal end;

wherein the imaging system is comprised of an imaging fiber bundle terminated in an objective lens system;

wherein each illumination system is comprised of an illumination fiber bundle terminated in an illumination lens system;

wherein the objective lens system is located at the central axis of said elongated cylindrical body structure;

wherein each illumination lens system is located below the central axis of said elongated cylindrical body structure toward the periphery of the elongated cylindrical metal body structure and oppositely placed with respect to the other illumination lens system to provide uniform and intense illumination of the pilot hole channel and the external outer periphery of the pedicle bone at infrared wavelengths; and wherein the irrigation and suction conduit is placed above the illumination system to end at an opening above the objective lens system;

wherein said fiber optics bundle assembly is comprised of an imaging fiber bundle encased in a plastic housing, two illumination fiber bundles encased in a plastic housing, and an irrigation and suction conduit;

wherein the imaging fiber bundle merges with the two illumination fiber bundles at a plastic-molded junction to emerge in a fiber optics assembly that encases individually the imaging fiber bundle and the two illumination fiber bundles in a synthetic material;

wherein the irrigation and suction conduit further merges with said fiber optics assembly at a plastic-molded junction to emerge in an integrated housing that encases individually the imaging fiber bundle, the two Illumination fiber bundles and the irrigation and suction conduit in a synthetic material and that enters said cylindrical merging structure as said single wire;

wherein said imaging fiber bundle in said fiber optics bundle assembly transitions to said imaging system in said elongated cylindrical metal body structure as the same imaging fiber bundle to provide imaging functions by connecting an imaging device to the proximal end of said fiber optics bundle assembly through one connector;

wherein each Illumination fiber bundle in the fiber optics bundle assembly further transitions to its corresponding illumination system in said elongated cylindrical metal body structure to provide Illumination functions by connecting an illumination device at the proximal end of said fiber optics bundle assembly through one connector;

wherein the irrigation and suction conduit in said fiber optics bundle assembly further transitions to said irrigation and suction conduit in said elongated cylindrical metal body structure to provide irrigation and suction functions by connecting irrigation and suction devices at the proximal end of said fiber optics bundle assembly through one connector;

wherein the fiber optics bundle assembly comprises flexible fiber optics bundles and said irrigation/suction conduit is flexible to allow for unobstructed manipulation of the endoscope with the handle;

wherein said endoscope is inserted in the proximal end of a multiaxial screwdriver cannula;

wherein said multiaxial screwdriver engages a pedicle screw at its distal end;

wherein said multiaxial screw driver is configured with spring-loaded balls near its proximal end in the inner wall of the cannula;

wherein said endoscope can exit said pedicle screw distal end through a pedicle screw cannula;

wherein the endoscope is configured with slots near the proximal end of the elongated metal body structure;

wherein the endoscope slots engage the spring-loaded balls in the inner wall of the cannula of the multiaxial screwdriver;

wherein the method for imaging with an endoscope, during an operation, comprises the steps of:

connecting the endoscope to imaging, illumination and irrigation/suction devices to enable its endoscopic functions at the selected wavelengths in the visible and infrared spectra, wherein said infrared wavelengths include wavelengths in the near infrared spectrum, the short wave infrared spectrum, the mid wave infrared spectrum or the long wave infrared spectrum;

inserting the endoscope in the multiaxial screwdriver proximal end cannula until it reaches the exit in the pedicle screw distal while being held in place with the slots;

screwing the pedicle screw a short distance into the pilot hole;

inserting the endoscope tip a short distance into the pilot hole;

continuing pedicle screw screwing into the pilot hole with the endoscope retained in place by the slots;

suctioning blood and flushing endoscope lenses as needed;

continually ascertaining with the endoscope whether the pedicle screw is in the right path without damage to pilot hole walls or outer nerve and vascular structures by viewing the monitor;

determining whether the pedicle screw is diverting from the pilot hole path and causing damage to walls or outer nerve and vascular structures;

withdrawing the pedicle screw a short distance if there is damage to pilot hole walls or outer nerve and vascular structures;

evaluating the extent of the damage to pilot hole walls and outer nerve and vascular structures with endoscope by viewing the monitor;

determining whether the pilot hole is too damaged;

withdrawing the pedicle screw if the pilot hole is too damaged;

stopping the operation after withdrawing the pedicle screw;

continuing the operation if there is no damage to the pilot hole walls or outer nerve and vascular structures;

determining during the operation whether the vertebral body has been reached;

disengaging the multiaxial screwdriver from the pedicle screw if the vertebral body has been reached;

stopping the operation with success if the vertebral body has been reached;

continuing the operation if the vertebral body has not been reached, whereby a pilot hole is imaged to determine its condition and thinness, and to determine said pilot hole wall breaches by said pedicle screw by operation at the selected visible and infrared light wavelengths, the operation at selected infrared wavelengths being performed for tissue transparency imaging of the pilot hole to determine the location of the nerve and vascular structures located on the outer surface of the pedicle bone.

5. A method for providing imaging to determine the condition of pilot holes with an endoscope, wherein the endoscope comprises:

an elongated cylindrical metal body structure having a proximal end and a distal end, wherein said distal end terminates on a plane perpendicular to said elongated cylindrical metal body structure axis;

a cylindrical merging structure of a predetermined length, configured for use as a handle and attached to said elongated cylindrical metal body proximal end by a conical support structure;

a fiber optics bundle assembly that enters said cylindrical merging structure as a single wire;

wherein said elongated cylindrical metal body structure is configured with a length and a diameter to traverse the length of the pilot hole;

an imaging system that runs along the longitudinal axis of said elongated cylindrical medal body structure including two illumination systems longitudinally parallel to and below the axis of said elongated cylindrical metal body structure located toward a periphery of said elongated cylindrical metal body structure;

an irrigation and suction conduit;

wherein the imaging system and illumination systems are terminated in an optical distal end of said elongated cylindrical metal body structure and are placed geometrically flush on said distal end;

wherein the imaging system is comprised of an imaging fiber bundle terminated in an objective lens system;

wherein each illumination system is comprised of an illumination fiber bundle terminated in an illumination lens system;

wherein the objective lens system is located at the central axis of said elongated cylindrical body structure;

wherein each illumination lens system is located below the central axis of said elongated cylindrical body structure toward the periphery of the elongated cylindrical metal body structure and oppositely placed with respect to the other illumination lens system to provide uniform and intense illumination of a channel of the pilot hole and the external outer periphery of the pedicle bone in the infrared spectrum; and wherein the irrigation and suction conduit is placed above the illumination system to end at an opening above the objective lens system;

wherein said fiber optics bundle assembly is comprised of the imaging fiber bundle encased in a plastic housing, the two illumination fiber bundles encased in a plastic housing, and the irrigation and suction conduit;

wherein the imaging fiber bundle merges with the two illumination fiber bundles at a plastic-molded junction to emerge in a fiber optics assembly that encases individually the imaging fiber bundle and the two Illumination fiber bundles in a synthetic material;

wherein the irrigation and suction conduit further merges with said fiber optics assembly at a plastic-molded junction to emerge in an integrated housing that encases individually the imaging fiber bundle, the two illumination fiber bundles and the irrigation and suction conduit in a synthetic material and that enters said cylindrical merging structure as said single wire;

wherein said imaging fiber bundle in said fiber optics bundle assembly transitions to said imaging system in said elongated cylindrical metal body structure as the same imaging fiber bundle to provide imaging functions by connecting an imaging device to the proximal end of said fiber optics bundle assembly through one connector;

wherein each illumination fiber bundle in the fiber optics bundle assembly further transitions to its corresponding illumination system in said elongated cylindrical metal body structure to provide illumination functions by connecting an illumination device at the proximal end of said fiber optics bundle assembly through one connector;

wherein the irrigation and suction conduit in said fiber optics bundle assembly further transitions to said irrigation and suction conduit in said elongated cylindrical metal body structure to provide irrigation and suction functions by connecting irrigation and suction devices at the proximal end of said fiber optics bundle assembly through one connector;

wherein the fiber optics bundle assembly comprises flexible fiber optics bundles and said irrigation/suction conduit is flexible to allow for unobstructed manipulation of the endoscope with the handle;

wherein the method for imaging with an endoscope, during an operation, comprises the steps of:

positioning the infrared endoscope at the pilot hole opening;

inserting the endoscope slowly into the pilot hole while viewing the operation in the monitor to determine the structural soundness of the pilot hole, the thinness of the pilot hole walls with respect to the outer surface of the pedicle bone and the location of the outer nerve and vascular structures;

continuing the slow insertion of the endoscope while viewing the monitor to determine the structural soundness of the pilot hole, the thinness of the pilot hole walls with respect to the outer surface of the pedicle bone and the location of the outer nerve and vascular structures until the end of the pilot hole is reached wherein the step of inserting the endoscope further includes inspecting the pilot hole selectively with illumination in the visible and infrared spectra from the opening of the pilot hole in the pedicle bone to the end of the pilot hole near the vertebra center, before the insertion of a pedicle screw in the pilot hole with a multiaxial screwdriver; and imaging the pilot hole for wall roughness or fractures selectively in the visible and infrared spectra, by imaging the thinness of the pilot hole walls and by imaging the proximity of the pedicle bone outer vascular and nerve structures in the infrared spectrum to ascertain whether the pilot hole is suitable for subsequent pedicle screw insertion, using a multiaxial screwdriver;

wherein said infrared spectrum includes the near infrared spectrum, the short wave infrared spectrum, the mid wave infrared spectrum and the long wave infrared spectrum.

* * * * *